United States Patent
Katsumoto et al.

(10) Patent No.: US 10,466,257 B2
(45) Date of Patent: Nov. 5, 2019

(54) MEASURING ELECTRICAL PROPERTIES OF A SAMPLE USING AN ELECTRICAL MEASURING CONTAINER

(71) Applicant: Sony Corporation, Tokyo (JP)

(72) Inventors: Yoichi Katsumoto, Tokyo (JP); Marcaurele Brun, Tokyo (JP); Yoshihito Hayashi, Chiba (JP)

(73) Assignee: Sony Corporation, Tokyo (JP)

( * ) Notice: Subject to any disclaimer, the term of this patent is extended or adjusted under 35 U.S.C. 154(b) by 832 days.

(21) Appl. No.: 14/095,657

(22) Filed: Dec. 3, 2013

(65) Prior Publication Data

US 2014/0162348 A1   Jun. 12, 2014

(30) Foreign Application Priority Data

Dec. 12, 2012  (JP) ................................ 2012-271612

(51) Int. Cl.
  *G01N 27/02* (2006.01)
  *G01N 33/86* (2006.01)
  *G01N 33/49* (2006.01)

(52) U.S. Cl.
  CPC ......... *G01N 33/86* (2013.01); *G01N 33/4905* (2013.01); *G01N 27/02* (2013.01)

(58) Field of Classification Search
  None
  See application file for complete search history.

(56) References Cited

U.S. PATENT DOCUMENTS

| | | | | |
|---|---|---|---|---|
| 3,840,806 A | * | 10/1974 | Stoner | G01N 27/07 324/443 |
| 4,319,194 A | * | 3/1982 | Cardinal | G01N 33/86 324/449 |
| 5,495,176 A | * | 2/1996 | Shiranita | G01N 27/07 204/422 |
| 5,837,199 A | * | 11/1998 | Dumschat | G01N 27/283 422/68.1 |

(Continued)

FOREIGN PATENT DOCUMENTS

| | | |
|---|---|---|
| CN | 1357300 A | 7/2002 |
| CN | 102308203 A | 1/2012 |

(Continued)

OTHER PUBLICATIONS

Office Action for JP Patent Application No. 2017-000489, dated Oct. 31, 2017, 05 pages of Office Action and 03 pages of English Translation.

(Continued)

*Primary Examiner* — Jill A Warden
*Assistant Examiner* — Brittany I Fisher
(74) *Attorney, Agent, or Firm* — Chip Law Group

(57) ABSTRACT

There is provided an electrical measuring container of a biological sample in a liquid phase, including at least a biological sample holding section configured to accommodate a biological sample in a liquid phase and made of a resin, and an electrical conductive section fixed to the biological sample holding section. In a state in which a portion of the electrical conductive section is buried in the biological sample holding section, the biological sample holding section and the electrical conductive section are integrally formed with each other.

20 Claims, 9 Drawing Sheets

1: ELECTRICAL MEASURING CONTAINER
2: BIOLOGICAL SAMPLE HOLDING SECTION
3: ELECTRICAL CONDUCTIVE SECTION
31: ELECTRODE SECTION
32: CONNECTING SECTION
S: BIOLOGICAL SAMPLE

(56) References Cited

U.S. PATENT DOCUMENTS

| | | | | |
|---|---|---|---|---|
| 8,008,063 B2* | 8/2011 | Ragsdale | ............... | C12M 35/02 204/403.01 |
| 2003/0011386 A1* | 1/2003 | Xie | ................... | G01N 33/2823 324/694 |
| 2006/0016701 A1* | 1/2006 | Qin | ................... | G01N 27/3335 205/792 |
| 2007/0140902 A1* | 6/2007 | Calatzis | ................. | G01N 27/07 422/400 |
| 2010/0099094 A1* | 4/2010 | Okada | ................... | C12Q 1/682 435/6.16 |
| 2011/0309848 A1* | 12/2011 | Eberheim | ............... | B22F 3/225 324/724 |
| 2014/0162348 A1 | 6/2014 | Katsumoto et al. | | |

FOREIGN PATENT DOCUMENTS

| | | |
|---|---|---|
| CN | 102435855 A | 5/2012 |
| CN | 102465094 A | 5/2012 |
| JP | 55-050162 A | 4/1980 |
| JP | 58-022946 A | 2/1983 |
| JP | 58-171655 A | 10/1983 |
| JP | 2004-522146 A | 7/2004 |
| JP | 2005-077148 A | 3/2005 |
| JP | 2007-304116 A | 11/2007 |
| JP | 2009-042141 | 2/2009 |
| JP | 2010-181400 | 8/2010 |
| JP | 2012-052906 | 3/2012 |
| WO | 91/09295 A1 | 6/1991 |

OTHER PUBLICATIONS

Office Action for JP Patent Application No. 2018-173691, dated Aug. 20, 2019, 03 pages of Office Action and 03 pages of English Translation.

Office Action for CN Patent Application No. 201711103781.7, dated Jul. 31, 2019, 12 pages of Office Action and 14 pages of English Translation.

* cited by examiner

1: ELECTRICAL MEASURING CONTAINER
2: BIOLOGICAL SAMPLE HOLDING SECTION
3: ELECTRICAL CONDUCTIVE SECTION
31: ELECTRODE SECTION
32: CONNECTING SECTION
S: BIOLOGICAL SAMPLE

1: ELECTRICAL MEASURING CONTAINER
2: BIOLOGICAL SAMPLE HOLDING SECTION
3: ELECTRICAL CONDUCTIVE SECTION
31: ELECTRODE SECTION
32: CONNECTING SECTION
S: BIOLOGICAL SAMPLE

1: ELECTRICAL MEASURING CONTAINER
2: BIOLOGICAL SAMPLE HOLDING SECTION
3: ELECTRICAL CONDUCTIVE SECTION
31: ELECTRODE SECTION
32: CONNECTING SECTION
S: BIOLOGICAL SAMPLE

1: ELECTRICAL MEASURING CONTAINER
2: BIOLOGICAL SAMPLE HOLDING SECTION
3: ELECTRICAL CONDUCTIVE SECTION
31: ELECTRODE SECTION
32: CONNECTING SECTION
S: BIOLOGICAL SAMPLE

1: ELECTRICAL MEASURING CONTAINER
2: BIOLOGICAL SAMPLE HOLDING SECTION
3: ELECTRICAL CONDUCTIVE SECTION
31: ELECTRODE SECTION
32: CONNECTING SECTION
33: HOLDING SECTION
34: BENDING SECTION
S: BIOLOGICAL SAMPLE

1: ELECTRICAL MEASURING CONTAINER
2: BIOLOGICAL SAMPLE HOLDING SECTION
3: ELECTRICAL CONDUCTIVE SECTION
31: ELECTRODE SECTION
32: CONNECTING SECTION
33: HOLDING SECTION
34: BENDING SECTION
S: BIOLOGICAL SAMPLE
10: ELECTRICAL MEASURING APPARATUS
4: APPLICATION UNIT
5: MEASUREMENT UNIT
6: ANALYSIS UNIT

MEASURING ELECTRICAL PROPERTIES OF A SAMPLE USING AN ELECTRICAL MEASURING CONTAINER

CROSS REFERENCES TO RELATED APPLICATIONS

The present application claims priority to Japanese Priority Patent Application JP 2012-271612 filed in the Japan Patent Office on Dec. 12, 2012, the entire content of which is hereby incorporated by reference.

BACKGROUND

The present application relates to an electrical measuring container configured to measure electrical properties of a biological sample in a liquid phase, and more particularly, an electrical measuring container having a structure configured to precisely measure electrical properties of a biological sample in a liquid phase and enabling easy industrial production, and an electrical measuring apparatus and an electrical measuring method using the electrical measuring container.

Measurement of electrical properties of a biological sample in a liquid phase, determination of physical properties of the sample from the measurement result, and discrimination of a kind of cell or the like included in the sample, and so on, are performed (for example, see Japanese Patent Application Laid-open No. 2009-042141). The measured electrical properties may be complex permittivity or frequency dispersion (a dielectric spectrum) thereof. The complex permittivity or the frequency dispersion is generally calculated by measuring a complex capacitance and complex impedance between electrodes using a solution retainer or the like including the electrodes configured to apply a voltage to a solution.

In addition, for example, in Japanese Patent Application Laid-open No. 2010-181400, a technology of obtaining information related to blood coagulation from permittivity of blood is disclosed, and "a blood coagulation system analysis device including a pair of electrodes, an application unit configured to apply an alternating current voltage to the pair of electrodes at predetermined time intervals, a measurement unit configured to measure the permittivity of the blood disposed between the pair of electrodes, and an analysis unit configured to analyze a level of function of the blood coagulation system using the permittivity of the blood measured at the time intervals after an action of the anticoagulant agent functioned in the blood is released" is disclosed.

When the electrical properties of the biological sample of the liquid phase are measured, as a container configured to accommodate the biological sample, for example, Japanese Patent Application Laid-open No. 2012-052906 discloses a sample cartridge having a cylindrical body made of an insulating material, configured to hold the liquid sample in a region including surfaces of electrodes inserted into an inner hole from both of end openings and a surface of the inner hole, and in which a constriction section disposed between the two opposite electrodes and formed by constricting the inner hole is installed at that region, measuring electrical properties of a liquid sample.

Here, in order to measure the electrical properties of the biological sample in the liquid phase, a measuring electrode should come in contact with the biological sample in the liquid phase. In the related art, measurement is performed in a state in which the biological sample in the liquid phase is accommodated in the container to which the measuring electrode is adhered and fixed. However, in this method, for example, when the electrical properties of the blood as a biological sample are measured, coagulation activity of the blood may be accelerated according to the kind of used adhesive agent, and may exert an influence on objective measurement.

In addition, even when an adhesive agent having low coagulability is temporarily used, since manufacturing processes for manufacturing the container are increased, productivity may be degraded.

Meanwhile, as a method not using the adhesive agent, for example, a method of measuring electrical properties in a state in which electrodes are inserted from the outside into a container configured to accommodate a biological sample is performed. However, in this method, a measurement error may occur due to a difference in insertion amount of the electrodes into the liquid sample.

In addition, since configurations of external apparatuses are increased, the apparatus is increased in size, the manufacturing process is complicated, and the apparatus is increased in price.

SUMMARY

As described above, when electrical measurement of the liquid sample is performed using the container to which the electrodes are previously adhered and fixed, the adhesive agent may exert an influence on a biological body material or productivity may be decreased. Meanwhile, in measurement using external electrodes, a measurement error may occur, the manufacturing process may be complicated, and the apparatus may be increased in price.

Here, it is desirable to provide an electrical measuring container including a structure configured to precisely measure electrical properties of a biological sample in a liquid phase and enabling industrial production.

The inventors of the application have diligently researched a structure of a container used when a biological sample in a liquid phase is measured, and devised a method of forming the container by focusing on not using the gluing agent, completing the present application.

That is, in the present application, first, there is provided an electrical measuring container of a biological sample in a liquid phase, which includes at least:

a biological sample holding section configured to accommodate the biological sample in the liquid phase and made of a resin; and an electrical conductive section fixed to the biological sample holding section, wherein, in a state in which a portion of the electrical conductive section is buried in the biological sample holding section, the biological sample holding section and the electrical conductive section are integrally formed with each other.

In the electrical measuring container according to the present application, since the electrical conductive section and the biological sample holding section are integrally formed with each other in a state in which the portion of the electrical conductive section is buried in the biological sample holding section, the electrical conductive section may be fixed to the biological sample holding section without using a gluing agent.

While a specific method of the integral forming is not particularly limited, for example, as the electrical conductive section is insert-formed in the biological sample holding section, the electrical conductive section and the biological sample holding section may be integrally formed with each other.

In the electrical measuring container according to the present application, the electrical conductive section may include at least an electrode section in contact with the biological sample upon measurement, and a connecting section configured to be electrically connected to an external circuit.

While the electrode section of the electrical conductive section may be freely disposed according to a purpose of measurement, for example, one or more pairs of electrode sections may be provided.

In addition, the electrode section may also be disposed to be included in a portion of an inner wall of the electrical measuring container. In this case, in the inner wall, a connecting section of the biological sample holding section and the electrode section may be smoothly configured.

Further, the electrode section may also be disposed to be positioned a predetermined distance above a portion that becomes a bottom section upon measurement.

In the electrical measuring container according to the present application, at least a portion of the electrical conductive section may function as a holding section configured such that the electrical conductive section is disposed at a predetermined place of the biological sample holding section upon the integral forming.

The biological sample configured to measure electrical properties using the electrical measuring container according to the present application may be, for example, a biological sample containing a sedimentary ingredient. More specifically, for example, a biological sample containing a blood ingredient may be provided.

When the electrical measuring container according to the present application is used for the electrical measurement of the biological sample containing the sedimentary ingredient, the electrode section may be disposed to be positioned above a position at which an accumulation sedimentation fraction of the sedimentary ingredient from the portion that becomes the bottom section upon measurement is equal to or larger than a volume fraction.

In the electrical measuring container according to the present application, a bending section may be installed at the portion buried in a biological sample holding section of the electrical conductive section.

While the kind of resin used in the electrical measuring container according to the present application is not particularly limited, for example, one or more kinds of resins selected from polypropylene, polystyrene, acryl and polysulfone may be used.

In addition, in the electrical measuring container according to the present application, while a material having electrical conductivity used in the electrical conductive section is not particularly limited, for example, an electrically conductive material containing titanium may be used.

While the electrical measuring container according to the present application may be used in all of the electrical measurements, for example, the electrical measuring container may be used to measure permittivity of the biological sample of impedance of the biological sample.

More specifically, when the biological sample including the blood ingredient is used, in order to measure a blood sedimentation situation or a blood coagulation situation, the electrical measuring container according to the present application may be used.

The electrical measuring container according to the present application may be appropriately used as a portion of an electrical measuring apparatus.

Specifically, there is provided an electrical measuring apparatus of a biological sample in a liquid phase, which includes at least:

a biological sample holding section configured to accommodate the biological sample in the liquid phase and made of a resin;

an electrical conductive section, at least a portion of which comes in contact with the biological sample upon measurement;

an application unit configured to apply a voltage to the electrical conductive section; and a measurement unit configured to measure electrical properties of the biological sample, wherein, in a state in which a portion of the electrical conductive section is buried in the biological sample holding section, the biological sample holding section and the electrical conductive section are integrally formed with each other.

In addition, the electrical measuring container according to the present application may be appropriately used in an electrical measuring method of a biological sample in a liquid phase.

According to one or more of embodiments of the electrical measuring container of the present application, the electrical conductive section is fixed to the biological sample holding section without using an adhesive agent. For this reason, the electrical properties of the biological sample in the liquid phase can be precisely measured without being influenced by an adhesive agent. In addition, since the electrical measuring container according to the present application can be easily manufactured, the electrical measuring container can be produced at a low cost in large quantities.

Additional features and advantages are described herein, and will be apparent from the following Detailed Description and the figures.

DETAILED DESCRIPTION

Figure 1:
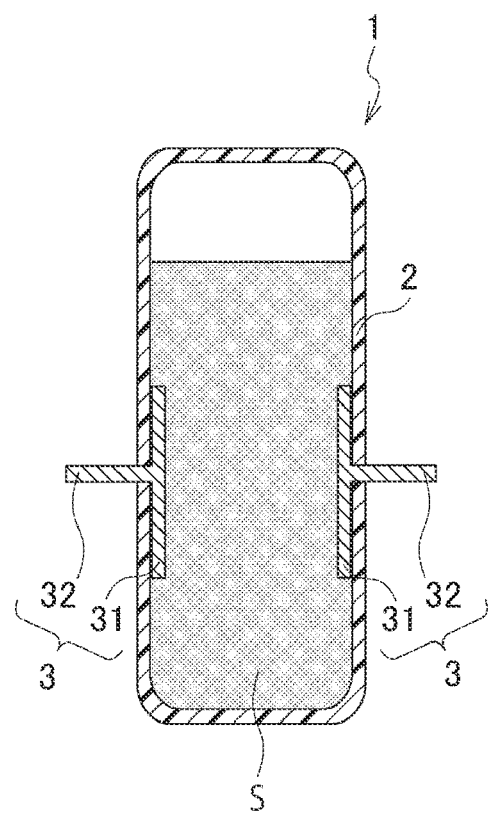
FIG. 1 is a schematic cross-sectional view schematically showing a first embodiment of an electrical measuring container 1 according to the present application.

Hereinafter, preferred modes for carrying out the present application will be described in detail with reference to the appended drawings. In addition, the embodiments to be described below are representative exemplary embodiments of the present application, and thus, the scope of the present application is not interpreted narrowly. Further, the description will be provided in the following sequence.

1. Electrical measuring container 1
(1) Biological sample holding section 2
(2) Electrical conductive section 3
(a) Electrode section 31
<First embodiment>
<Second embodiment>
<Third embodiment>
<Fourth embodiment>
(b) Connecting section 32
(c) Holding section 33
<Fifth embodiment>
(d) Bending section 34
<Sixth embodiment>
(3) Biological sample S
(4) Others
2. Electrical measuring apparatus 10
(1) Application unit 4
(2) Measurement unit 5
(3) Analysis unit 6
3. Electrical measuring method 1. Electrical Measuring Container 1

FIG. 1 is a schematic cross-sectional view schematically showing a first embodiment of an electrical measuring container 1 according to the present application. The electrical measuring container 1 according to the present application is a container used to hold a biological sample in a liquid phase when electrical properties of the biological sample are measured. The electrical measuring container 1 according to the present application generally includes at least a biological sample holding section 2 and an electrical measuring container conductive section 3. Hereinafter, the respective parts will be described in detail. In addition, in the respective drawings, for the purpose of the description, while a biological sample S is shown, the biological sample S is not included in the electrical measuring container 1 according to the present application.

(1) Biological Sample Holding Section 2

The biological sample holding section 2 is an area in which a liquid phase biological sample of a measurement target is held. In the electrical measuring container 1 according to the present application, the biological sample holding section 2 is characterized to be made of a resin.

In the electrical measuring container 1 according to the present application, the kind of resin used in the biological sample holding section 2 is not particularly limited, and one or two or more kinds of resins that can be appropriately applied to the biological sample in the liquid phase may be freely selected and used. For example, a hydrophobic and insulating polymer such as polypropylene, polymethyl methacrylate, polystyrene, acryl, polysulfone, polytetrafluoroethylene, or the like, a copolymer, a blend polymer or the like may be used. In the present application, in the above-mentioned polymers, in particular, the biological sample holding section 2 may be made of one or more kinds of resins selected from polypropylene, polystyrene, acryl, and polysulfone. Since these resins have a property such as a low coagulation activity with respect to the blood, for example, the container can be appropriately used for measurement of the biological sample containing the blood.

In the electrical measuring container 1 according to the present application, a specific shape of the biological sample holding section 2 is not particularly limited, and a cylindrical body, a polygonal cylindrical body having a polygonal (triangular, rectangular, etc.) cross-section, a circular conical body, a polygonal conical body having a polygonal (triangular, rectangular, etc.) cross-section, or a combined shape of one or two or more cross-sections, may be freely designed according to the kind of biological sample S, a measuring method, a used measurement, or the like, as long as the biological sample S in the liquid phase can be held.

In a state in which the biological sample S in the liquid phase is held in the biological sample holding section 2, measurement of various kinds of electrical properties is performed. For this reason, the biological sample holding section 2 may be configured to be sealable in a state in which the biological sample S is held. However, a time to measure the various kinds of electrical properties of the biological sample S in the liquid phase may be delayed, and the section may not be configured to be hermetically sealed as long as the measurement is not influenced.

A specific introducing and sealing method of the biological sample S in the liquid phase to the biological sample holding section 2 is not particularly limited and the biological sample S can be freely introduced according to the shape of the biological sample holding section 2. For example, while not shown, a method of installing a lid section at the biological sample holding section 2, introducing the biological sample S using a pipette or the like, and then closing and sealing the lid section, or a method of inserting an injection needle from an outer surface of a biological sample holding section, injecting the biological sample S in the liquid phase, and then closing and sealing an area penetrated by the injection needle with grease or the like, may be provided.

(2) Electrical conductive section 3

In the electrical measuring container 1 according to the present application, the electrical conductive section 3 is characterized in that it is previously fixed to the biological sample holding section 2. In particular, in the present application, in a state in which a portion of the electrical conductive section 3 is buried in the biological sample holding section 2, the biological sample holding section 2 and the electrical conductive section 3 are configured to be integrally formed with each other. That is, no fixing material such as an adhesive agent or the like is used in fixing of the biological sample holding section 2 and the electrical conductive section 3.

When the fixing is performed using an adhesive agent, properties of the biological sample S may be influenced according to the kind of adhesive agent used. For example, when electrical properties of the blood as the biological sample S are measured, coagulation activity of the blood may be accelerated according to the kind of adhesive agent used, and may exert an influence on the desired measurement. However, in the electrical measuring container 1 according to the present application, since the adhesive agent is not used to fix the biological sample holding section 2 and the electrical conductive section 3, the influence on the biological sample S by the adhesive agent can be excluded. As a result, the electrical properties of the biological sample S can be precisely measured.

In addition, even when an adhesive agent having a small influence on the biological sample S is temporarily used, since an adhering process is increased due to the adhesive agent when the container is manufactured, productivity may be degraded. However, in the manufacturing process of the electrical measuring container 1 according to the present application, since the biological sample holding section 2 and the electrical conductive section 3 are integrally formed with each other, the adhering does not have to be separately provided in addition to the forming process of the biological sample holding section 2. As a result, the electrical measuring container 1 can be easily manufactured, and the electrical measuring container 1 can be produced at a low cost in large quantities.

Meanwhile, as the method using no adhesive agent, for example, a method of measuring electrical properties in a state in which electrodes are inserted from the outside into a container configured to accommodate a biological sample is provided. In this method, a measurement error may occur due to a difference in insertion amount of the electrodes into the liquid sample. However, in the electrical measuring container 1 according to the present application, the electrical conductive section 3 is previously fixed to the biological sample holding section 2. For this reason, as will be described below, as the electrical conductive section 3 is used as the electrode, the measurement error due to the difference in insertion amount of the electrodes into the liquid sample can be removed. As a result, the electrical properties of the biological sample S can be precisely measured.

In addition, as the electrical conductive section 3 is previously fixed to the biological sample holding section 2, a relative positioning mechanism or the like between the electrode and the container may not be installed at the side of the apparatus, and the apparatus may be simply configured. As a result, this contributes to realization of miniaturization of the apparatus, simplification of the manufacturing process, a low cost of the apparatus, and the like.

Further, since the number of parts of the electrical measuring container 1 can be reduced, user convenience can also be improved.

A specific method of integrally forming the biological sample holding section 2 and the electrical conductive section 3 is not particularly limited, and in a state in which a portion of the electrical conductive section 3 is buried in the biological sample holding section 2, as long as the biological sample holding section 2 and the electrical conductive section 3 can be fixed without using an adhesive agent, a free method can be used. For example, when the resin forming the biological sample holding section 2 is solidified from a melted state, as the electrical conductive section 3 is disposed at a predetermined position, the biological sample holding section 2 and the electrical conductive section 3 can be integrally formed with each other. As a more specific method, for example, the biological sample holding section 2 and the electrical conductive section 3 can be integrally formed by inserting the electrical conductive section 3 into a mold and injecting the resin around the electrical conductive section 3 to integrate the electrical conductive section 3 and the resin, which is known as insert molding.

In this way, in the electrical measuring container 1 according to the present application, when the biological sample holding section 2 is formed, since the electrical conductive section 3 is simultaneously fixed, the manufacturing process can be simplified. As a result, the electrical measuring container 1 can be produced at a low cost in large quantities.

The electrical conductive section 3 is made of a material having electrical conductivity. In the electrical measuring container 1 according to the present application, the kind of material having electrical conductivity used in the electrical conductive section 3 is not particularly limited, and one or two or more kinds of materials that can be appropriately applied to electrical measurement of the biological sample S in the liquid phase can be freely selected and used. For example, titanium, aluminum, stainless steel, platinum, gold, copper, graphite, or the like may be used. In the present application, among the materials, in particular, the electrical conductive section 3 may be made of a material having electrical conductivity and including titanium. Since titanium has a property such as a low coagulation activity with respect to the blood, for example, titanium can be appropriately used for measurement of the biological sample containing the blood.

The electrical conductive section 3 includes an electrode section 31 and a connecting section 32. In addition, according to necessity, a holding section 33 and a bending section 34 may be further provided. Hereinafter, the respective parts will be described in detail.

(a) Electrode Section 31

The electrode section 31 comes in contact with the biological sample S upon measurement to be used to apply a voltage desired for the biological sample S. In the electrical measuring container 1 according to the present application, the number of electrode sections 31 may be freely designed according to a desired electrical measuring method or the like. For example, when permittivity or impedance of the biological sample S is measured, one or more pairs of electrode sections 31 may be installed.

In addition, when a disposition, shape or the like of the electrode section 31 is not particularly limited and the voltage for the biological sample S can be applied, the electrode section 31 can be freely designed according to the desired electrical measuring method or the like. Hereinafter, an example of disposition of the electrode section 31 will be disposed in detail.

<First Embodiment>

The first embodiment shown in FIG. 1 is an example in which the pair of electrode sections 31 are disposed along an inner wall of the biological sample holding section 2. More specifically, for example, in a state in which a portion of the electrical conductive section 3 is buried in a sidewall of the biological sample holding section 2, the electrode section 31 is disposed inside the biological sample holding section 2 and the connecting section 32 (to be described below) is disposed outside the biological sample holding section 2. The electrode section 31 is disposed in vicinity of a center of the sidewall of the biological sample holding section 2.

<Second Embodiment>

Figure 2:
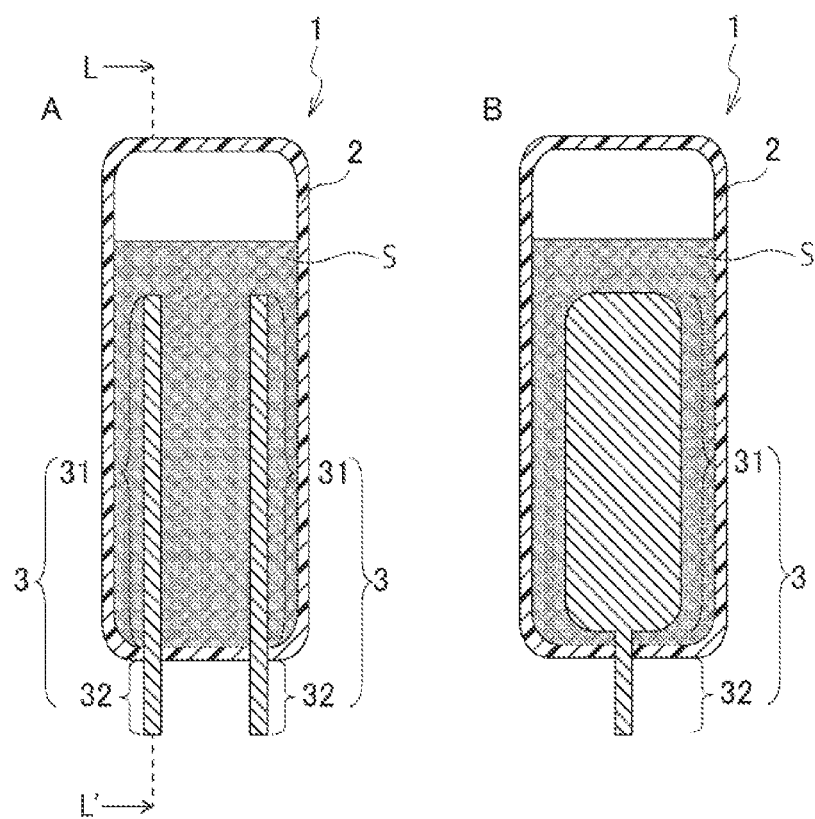
FIG. 2A is a schematic cross-sectional view schematically showing a second embodiment of the electrical measuring container 1 according to the present application.
FIG. 2B is a cross-sectional view taken along line L-L' of FIG. 2A.

FIG. 2A is a schematic cross-sectional view schematically showing a second embodiment of the electrical measuring container 1 according to the present application, and FIG. 2B is a cross-sectional view taken along line L-L' of FIG. 2A. The second embodiment is an example in which the pair of electrical conductive sections 3 are disposed in a state protruding from a bottom wall section of the biological sample holding section 2. More specifically, for example, in a state in which a portion of the electrical conductive section 3 is buried in the bottom wall section of the biological sample holding section 2, the electrode section 31 is disposed inside the biological sample holding section 2 and the connecting section 32 (to be described below) is disposed outside the biological sample holding section 2.

In the embodiment, a shape of the electrode section 31 is not particularly limited, and the electrode section 31 can be freely designed according to the shape of the biological sample holding section 2 or a desired electrical measuring method. In the present disclosure, in particular, in order to improve measurement efficiency, the electrode section 31 may come in surface contact with the liquid sample. As a specific shape, as shown in FIG. 2B, as a portion of the electrode section 31 in contact with the liquid sample is increased, the electrode section 31 can come in surface contact with the liquid sample.

<Third Embodiment>

Figure 3:
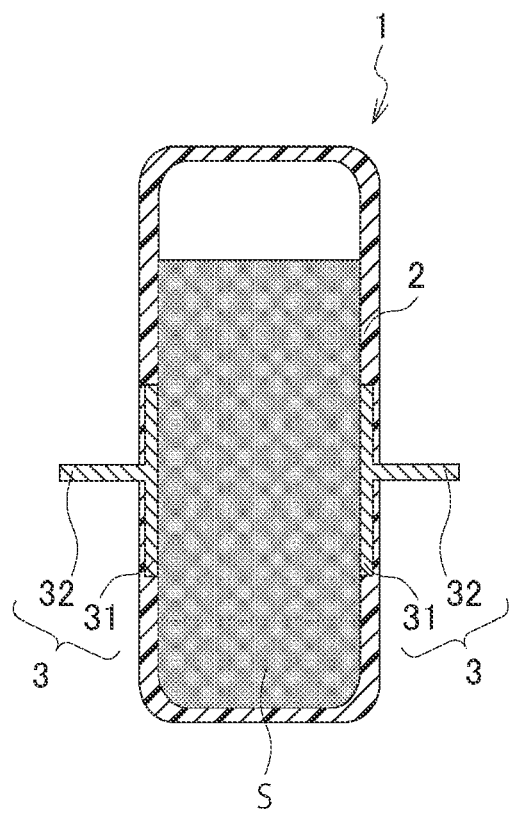
FIG. 3 is a schematic cross-sectional view schematically showing a third embodiment of the electrical measuring container 1 according to the present application.

FIG. 3 is a schematic cross-sectional view schematically showing a third embodiment of the electrical measuring container 1 according to the present application. The third embodiment is an example in which the pair of electrode sections 31 is included in a portion of the inner wall of the electrical measuring container 1. More specifically, for example, in a state in which a portion of the electrode section 31 is buried in a sidewall of the biological sample holding section 2, the electrode section 31 is disposed as a portion of the inner wall of the electrical measuring container 1 and the connecting section 32 (to be described below) is disposed outside the biological sample holding section 2.

In this way, when the electrode section 31 is disposed to be included in a portion of the inner wall of the electrical measuring container 1, as described in the third embodiment shown in FIG. 3, a connecting section of the biological sample holding section 2 and the electrode section 31 may be smoothly and integrally formed. In the case of the biological sample S in the liquid phase, when a step difference occurs in the container, bubbles or the like may remain therein, which may influence the measurement value. However, as the container is configured not to generate a step difference or the like at a boundary between the biological sample holding section 2 and the electrode section 31, retention of bubbles or the like can be prevented, and as a result, the electrical properties of the biological sample S can be more precisely measured.

In addition, when the one or more pairs of electrode sections 31 are provided, the electrode sections 31 may be disposed in parallel while measuring the electrical properties of the biological sample S. However, for example, in consideration of release characteristics or the like when the insert molding or the like is performed, the respective electrode sections 31 can be disposed in a state in which several inclinations are provided.

<Fourth Embodiment>

Figure 4:
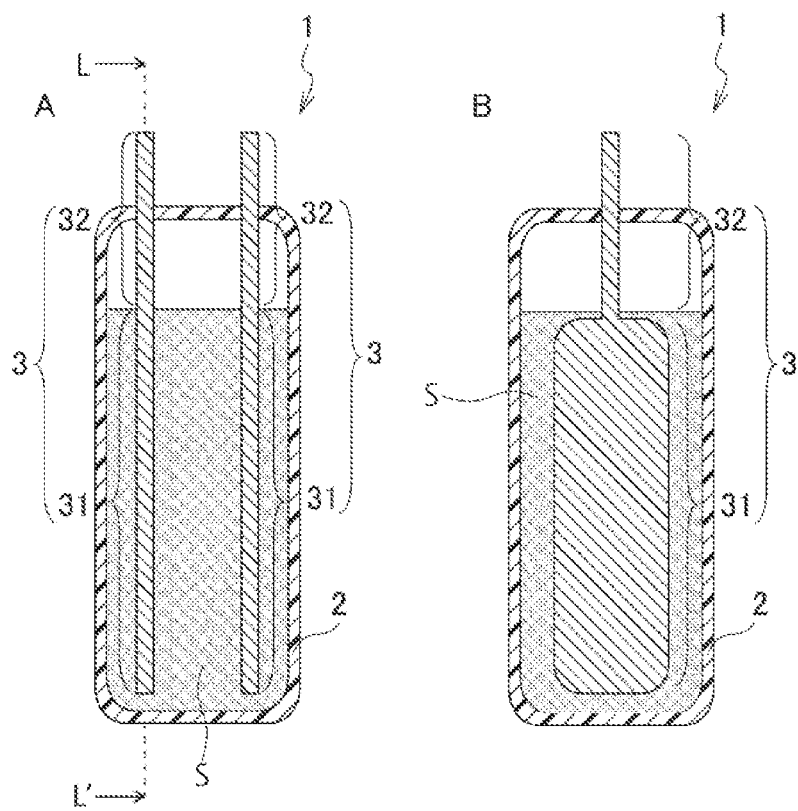
FIG. 4A is a schematic cross-sectional view schematically showing a fourth embodiment of the electrical measuring container 1 according to the present application.
FIG. 4B is a cross-sectional view taken along line L-L' of FIG. 4A.

FIG. 4A is a schematic cross-sectional view schematically showing a fourth embodiment of the electrical measuring container 1 according to an embodiment of the present application, and FIG. 4B is a cross-sectional view taken along line L-L' of FIG. 4A. The fourth embodiment is an example in which the pair of electrical conductive sections 3 are disposed to protrude from an upper wall section of the biological sample holding section 2. More specifically, for example, in a state in which a portion of the electrical conductive section 3 is buried in the upper wall section of the biological sample holding section 2, the electrode section 31 is disposed inside the biological sample holding section 2 and the connecting section 32 (to be described below) is disposed outside the biological sample holding section 2. As the electrical conductive section 3 protrudes from the upper wall section of the biological sample holding section 2, for example, in comparison with the embodiment in which the electrical conductive section 3 protrudes from the bottom wall section as described in the above-mentioned second embodiment, leakage of the sample can be more reliably prevented.

In the embodiment, a shape of the electrode section 31 is not particularly limited, and the electrode section 31 may be freely designed according to a shape of the biological sample holding section 2 or a desired electrical measuring method. For example, similar to the above-mentioned second embodiment, as a portion of the electrode section 31 in contact with the liquid sample is increased (see FIG. 4B), when the electrode section 31 is designed to come in surface contact with the liquid sample, measurement efficiency can be improved.

The electrical measuring container 1 according to the first, third or fourth embodiment is characterized in that the electrode section 31 is disposed a predetermined distance above a portion that becomes a bottom section upon measurement. For example, as will be described below, when the biological sample containing the sedimentary ingredient is used as the biological sample S, as the electrode section 31 is disposed a predetermined distance above the portion that becomes the bottom section upon measurement, a time-elapsed influence on the sedimentary ingredient due to the sedimentation can be suppressed. As a result, the electrical properties of the biological sample S can be more precisely measured.

Figure 5:
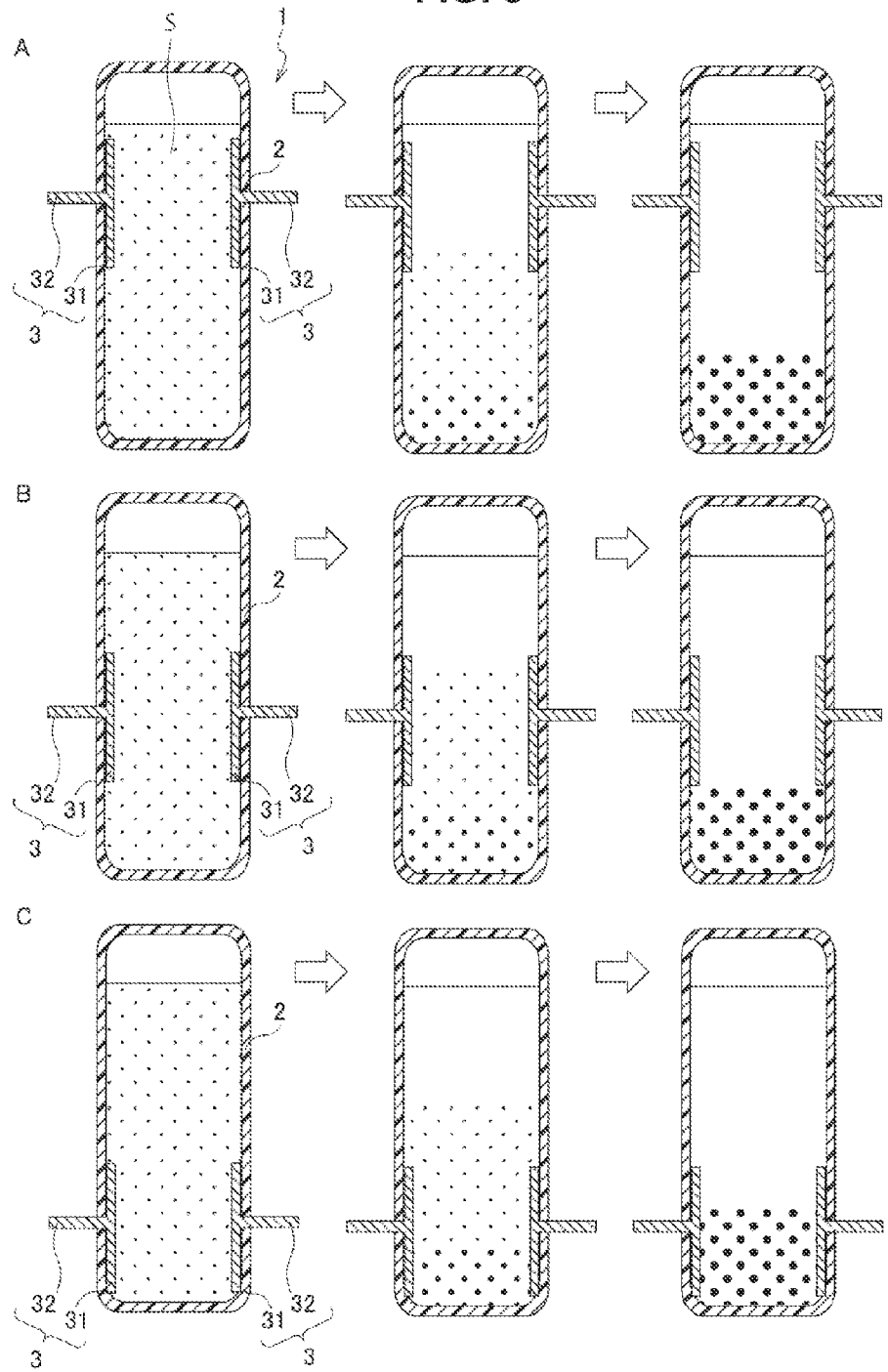
FIGS. 5A-C is a schematic cross-sectional view schematically showing a relation between an aspect of time-elapsed sedimentation of a sedimentary ingredient and a position of an electrode section 31 when a biological sample S containing a sedimentary ingredient is used.
Figure 6:
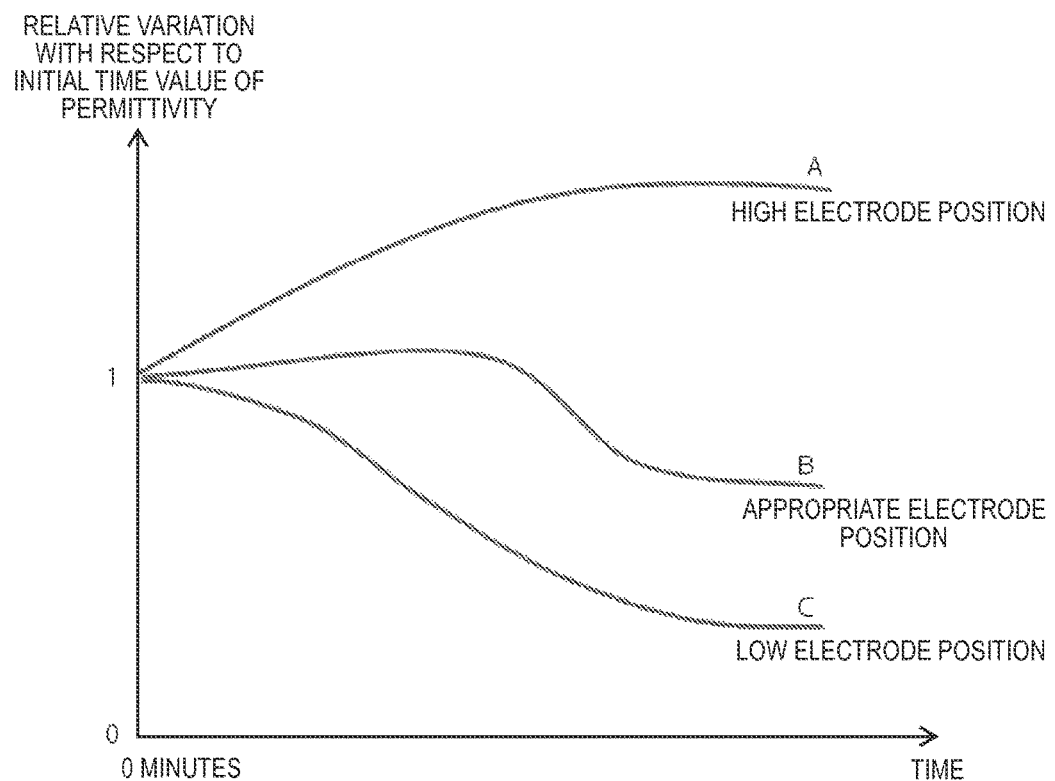
FIG. 6 is a graph showing an example of a relation between the position of the electrode section 31 corresponding to FIG. 5 and a measurement value when permittivity is measured.

Appropriate positioning of the electrode section 31 when the biological sample S containing the sedimentary ingredient is used will be described with reference to FIGS. 5 and 6. FIG. 5 is a schematic cross-sectional view schematically showing a relation between an aspect of time-elapsed sedimentation of the sedimentary ingredient and a position of the electrode section 31 when the biological sample S containing the sedimentary ingredient is used. FIG. 6 is a graph showing an example of a relation between the position of the electrode section 31 corresponding to FIG. 5 and a measurement value when permittivity is measured.

For example, as shown in FIG. 5B, when the electrode section 31 is disposed to be positioned a predetermined distance above the portion that becomes the bottom section upon measurement, as shown in FIG. 6B, a certain interval from the measurement shows a certain permittivity. As shown in FIG. 5B, this is because, even with the time-elapsed sedimentation of the sedimentary ingredient, a concentration of the sedimentary ingredient in a region narrowed at the pair of electrode sections 3 does not substantially vary up to a certain time.

Meanwhile, as shown in FIG. 5A, when the electrode section 31 is disposed at a high position, as shown in FIG. 6A, permittivity is increased immediately after the measurement starts. This is because, as shown in FIG. 5A, the concentration of the sedimentary ingredient in the region narrowed at the pair of electrode sections 31 is reduced by advance of the sedimentation of the sedimentary ingredient immediately after the measurement starts.

In addition, as shown in FIG. 5C, when the electrode section 31 is disposed at a low position, as shown in FIG. 6C, permittivity is lowered immediately after the measurement starts. This is because, as shown in FIG. 5C, the concentration of the sedimentary ingredient in the region narrowed at the pair of electrode sections 31 is increased by advance of the sedimentation of the sedimentary ingredient immediately after the measurement starts.

In this way, as shown in FIG. 5B, as the electrode section 31 is disposed a predetermined distance above the portion that becomes the bottom section upon measurement, even when the sedimentation of the sedimentary ingredient progresses in the biological sample S, precise measurement can be performed without influencing the measurement value in the middle of the sedimentation (see FIG. 6B). As a more specific position, the electrode section 31 may be disposed to be positioned above a position at which an accumulation sedimentation fraction of the sedimentary ingredient from the portion that becomes the bottom section upon measurement is equal to or larger than a volume fraction. When disposed at such a position, precise measurement can be performed for a longer time.

In addition, a relative variation of permittivity of a graph of FIG. 6 merely shows an example, and the variation may differ according to the kind of the biological sample S of the measurement target.

As an example of the biological sample S containing the sedimentary ingredient, the case in which whole blood is used as a measurement target will be described. In the case of a healthy adult human, the whole blood includes red blood cells of a volume fraction of about 40%. The red blood cells are deposited under a settling condition, and finally precipitated at a lower portion of the container. Meanwhile, serums are mainly collected on an upper layer section. During progress of the sedimentation process, three layers of a red blood cell precipitation layer, a whole blood layer and a serum layer are generally provided from a lower side thereof.

When the whole blood is used as the measurement target, the electrode section 31 may be disposed such that the measurement of the whole blood is performed for a long time as much as possible. Specifically, most lines of electric force emitted from the electrode section 31 and passing through a target sample may be disposed to continuously pass through the whole blood layer while avoiding the red blood cell precipitation layer and the serum layer sequentially generated in the container. As a specific disposition satisfying this, the electrode section 31 may be disposed such that a lower limit of the electrode section 31 is disposed above a position at which an accumulated volume fraction from the lower side is equal to or larger than a red blood cell volume fraction. In addition, the electrode section 31 may be disposed such that an upper limit of the electrode section 31 is disposed under the lower limit of the serum layer when a minimal time for the measurement elapses.

(b) Connecting Section 32

The connecting section 32 is an area electrically connected to an external circuit. A specific shape of the connecting section 32 is not particularly limited, and the connecting section 32 can be designed in a free shape as long as the connecting section comes in electrical contact with the external circuit.

(c) Holding section 33

<Fifth Embodiment>

Figure 7:
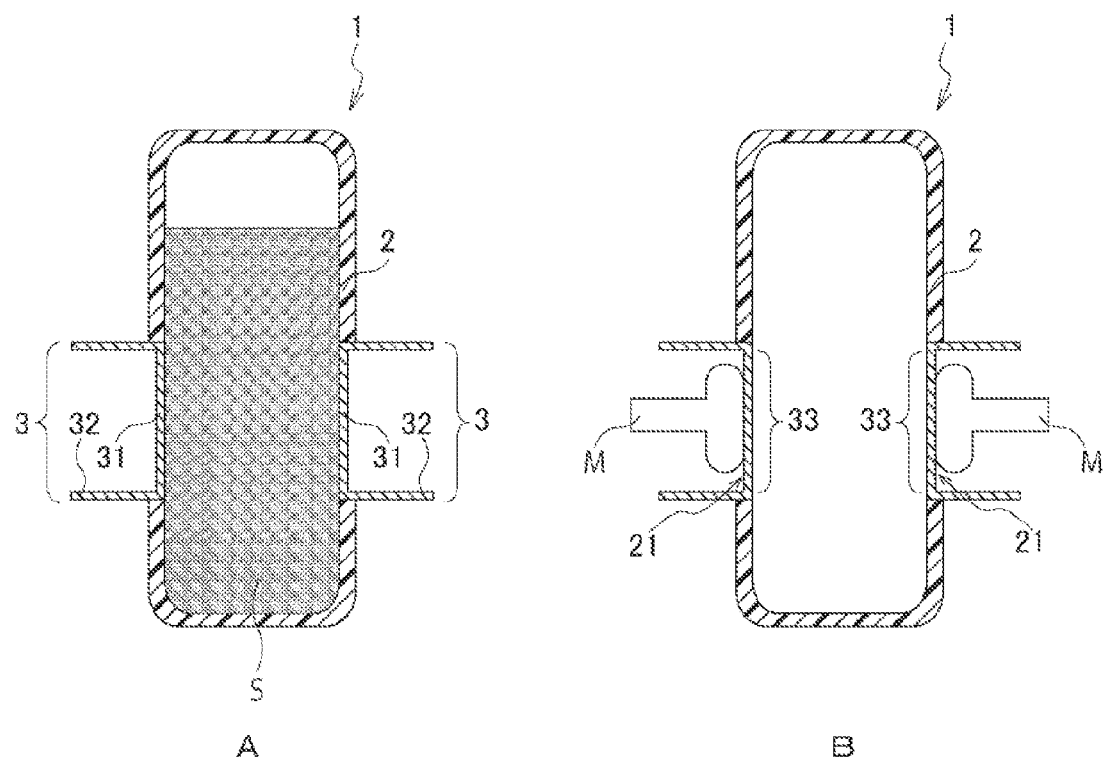
FIG. 7 is a schematic cross-sectional view schematically showing a fifth embodiment of the electrical measuring container 1 according to the present application.

FIG. 7 is a schematic cross-sectional view schematically showing a fifth embodiment of the electrical measuring container 1 according to an embodiment of the present application. The fifth embodiment is a configuration that does not include a resin at a portion of the pair of electrode sections 31 outside the container. According to the above-mentioned configuration, for example, upon formation of the biological sample holding section 2, as the electrical conductive section 3 is positioned and fixed using, for example, a magnet M or the like, the electrical conductive section 3 (in particular, the electrode section 31) can be positioned at a desired position of the electrical measuring container 1 (see FIG. 7B).

In addition, a fixing unit from the outside of the container is not limited to the magnet M shown in FIG. 7B, and any unit may be used as long as the fixing unit can fix the electrical conductive section 3 from the outside of the container.

In this way, as at least a portion of the electrical conductive section 3 functions as the holding section 33 such that the electrical conductive section 3 is disposed at a predetermined place of the biological sample holding section 2 upon integral forming, the electrical measuring container 1 in which the electrical conductive section 3 is positioned at a desired place can be easily manufactured.

In addition, upon formation of the biological sample holding section 2, as the electrical conductive section 3 is held, deformation of the electrical conductive section 3 upon integral forming can be prevented.

Further, in the fifth embodiment shown in FIG. 7, while the electrode section 31 is configured to simultaneously function as the holding section 33, the present application is not limited thereto. For example, the connecting section 32 may also be designed to simultaneously function as the holding section 33.

(d) Bending Section 34

<Sixth Embodiment>

Figure 8:
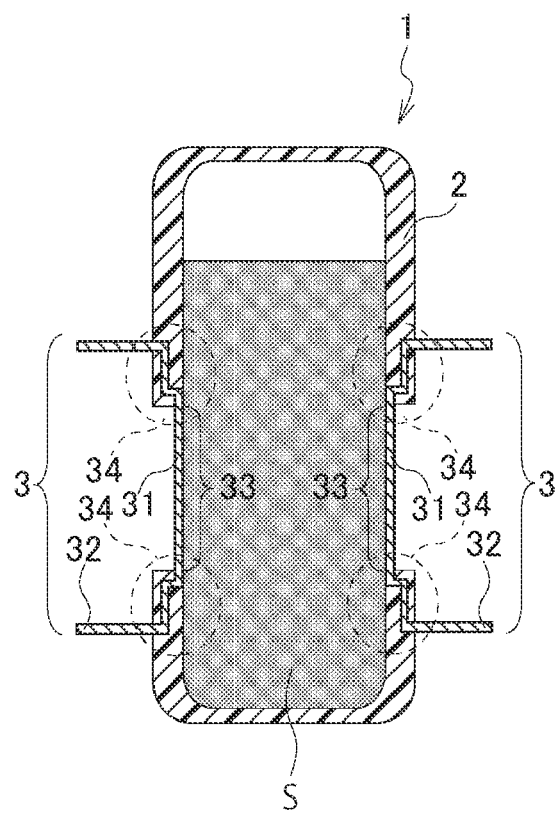
FIG. 8 is a schematic cross-sectional view schematically showing a sixth embodiment of the electrical measuring container 1 according to the present application.

FIG. 8 is a schematic cross-sectional view schematically showing a sixth embodiment of the electrical measuring container 1 according to an embodiment of the present application. The sixth embodiment is characterized in that the bending section 34 is provided at a portion of the electrical conductive section 3 buried in the biological sample holding section 2.

Since the electrical measuring container 1 according to an embodiment of the present application is characterized in that the biological sample holding section 2 and the electrical conductive section 3 are integrally formed without using an adhesive agent or the like, leakage of the biological sample S in the liquid phase from a boundary between the biological sample holding section 2 and the electrical conductive section 3 is extremely rare. However, according to storage conditions or measurement conditions such as a temperature or the like due to a difference in distortion between the resin and the electrical conductive material or the like, leakage of the biological sample S in the liquid phase from the boundary between the biological sample holding section 2 and the electrical conductive section 3 may occur. Here, like the sixth embodiment shown in FIG. 8, as the bending section 34 is provided at the portion buried in the biological sample holding section 2 of the electrical conductive section 3, for example, in comparison with the fifth embodiment (see FIG. 7) that does not include the bending section 34, leakage of the biological sample S from the boundary between the biological sample holding section 2 and the electrical conductive section 3 can be prevented.

In addition, as the bending section 34 is provided at the portion buried in the biological sample holding section 2 of the electrical conductive section 3, since the biological sample holding section 2 and the electrical conductive section 3 are more strongly fixed, the electrical measuring container 1 can have a stronger structure.

(3) Biological Sample S

The biological sample S that can be used as the measurement target in the present application is not particularly limited as long as the sample is in a liquid phase, and may be freely selected. For example, the biological sample S containing a sedimentary ingredient or the like may be provided. More specifically, the biological sample S containing blood ingredients such as whole blood, blood plasma, a diluted solution thereof, and/or drug additives, or the like, may be provided.

(4) Others

A predetermined drug may also be previously input into the electrical measuring container 1 according to an embodiment of the present application. For example, when the biological sample S containing the blood ingredient is used as a measurement target, an anticoagulant agent, a coagulation initiator, or the like, may be previously input into the biological sample holding section 2 of the electrical measuring container 1.

The electrical measuring container 1 according to an embodiment of the present application can be produced at a low cost in large quantities as described above. Using these characteristics, for example, the electrical measuring container 1 according to an embodiment of the present application may be a disposable cartridge. As the disposable cartridge is used as the electrical measuring container 1 according to an embodiment of the present application, effort of cleaning the container or the like can be reduced, and the measurement can be efficiently performed. In addition, generation of a measurement error or the like due to a separate biological sample S remaining in the container can be prevented, and the electrical properties of the biological sample S can be more precisely measured.

2. Electrical Measuring Apparatus 10

Figure 9:
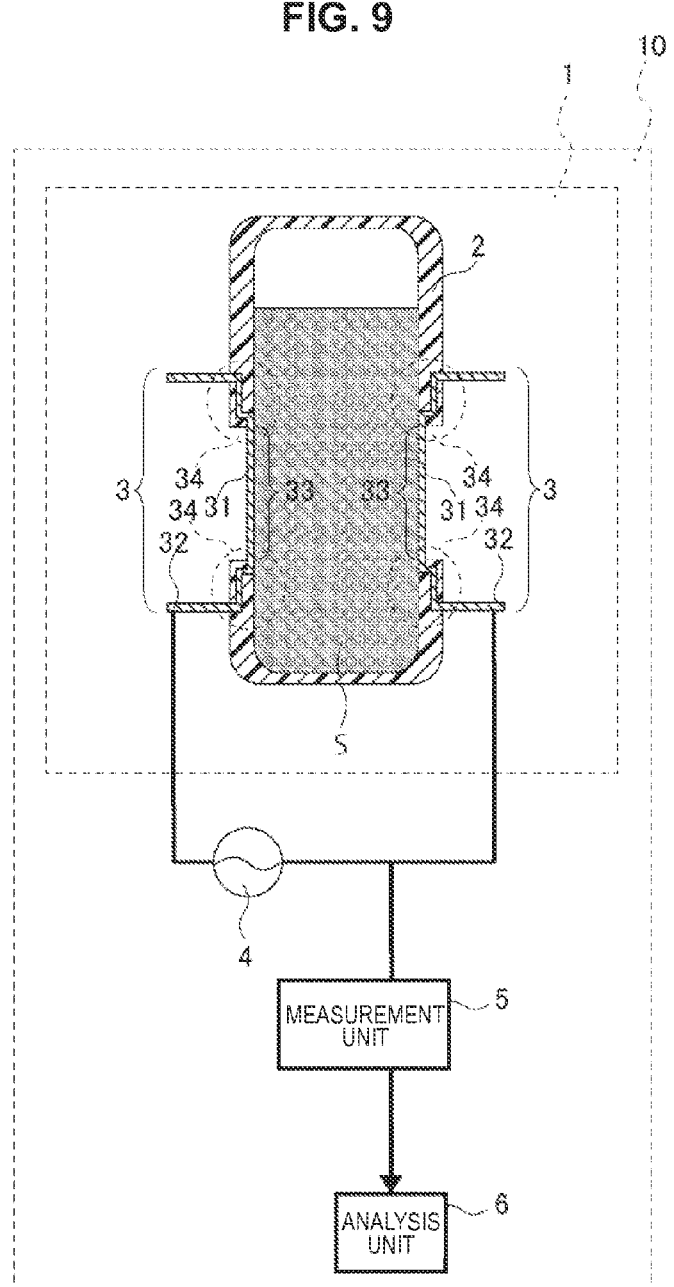
FIG. 9 is a schematic view schematically showing a first embodiment of an electrical measuring apparatus 10 according to the present application.

FIG. 9 is a schematic view schematically showing the first embodiment of an electrical measuring apparatus 10 according to an embodiment of the present application. In the embodiment, the electrical measuring container 1 according to the above-mentioned sixth embodiment is used. The electrical measuring apparatus 10 according to an embodiment of the present application generally includes at least the above-mentioned electrical measuring container 1, an application unit 4 and a measurement unit 5. In addition, according to necessity, an analysis unit 6 may further provided. Hereinafter, the respective parts will be described in detail. In addition, since the electrical measuring container 1 is similar to that described above, the description thereof will be omitted.

(1) Application Unit 4

The application unit 4 applies a voltage to the electrical conductive section 3 of the electrical measuring container 1 according to an embodiment of the present application. The application unit 4 applies a voltage to the electrical conductive section 3 of the electrical measuring container 1 when an order to initiate measurement is received or when power of the electrical measuring apparatus 10 is input as a start point. More specifically, the application unit 4 applies an alternating current voltage having a predetermined frequency to the electrical conductive section 3 at a set measurement interval. In addition, the voltage applied by the application unit 4 may be a direct current voltage according to the measured electrical properties.

(2) Measurement Unit 5

The measurement unit 5 measures electrical properties of the biological sample S in the liquid phase held in the electrical measuring container 1 according to an embodiment of the present application. Specifically, electrical properties such as complex permittivity (hereinafter simply referred to as "permittivity"), frequency dispersion thereof, or the like, are measured when an order to initiate measurement is received or when power of the electrical measuring apparatus 10 is input. More specifically, for example, when the permittivity is measured, the measurement unit 5 measures a current or impedance between the electrode sections 31 of the electrical measuring container 1 at a predetermined period, and derives permittivity from the measured value. In deriving the permittivity, a known function or relational expression showing a relation between the current or impedance and the permittivity may be used.

(3) Analysis Unit 6

The analysis unit 6 receives electrical property data of the biological sample S derived from the measurement unit 5, and performs determination or the like of physical properties of the biological sample S. In the electrical measuring apparatus 10 according to an embodiment of the present application, the analysis unit 6 may be omitted, and for example, the measurement unit 5 may perform analysis from the measured electrical property data using an external computer or the like.

Specifically, the electrical property data of the biological sample S derived from the measurement unit 5 is provided to the analysis unit 6 at measurement intervals, and the analysis unit 6 receives the electrical property data provided from the measurement unit 5 and starts determination or the like of the physical properties of the liquid sample. The analysis unit 6 informs of a result of the determination or the like of the physical properties of the liquid sample and/or permittivity data. The information may be converted into, for example, a graph to be displayed on a monitor or printed on a predetermined medium.

3. Electrical Measuring Method

The electrical measuring container 1 according to an embodiment of the present application may be appropriately used to measure the electrical properties of the biological sample S in the liquid phase. The electrical properties that can be measured through an electrical measuring method according to an embodiment of the present application are not particularly limited but may be freely measured according to the kind of the biological sample S, which is the measurement target, or physical properties to be analyzed. For example, permittivity, impedance, or the like, can be measured.

Using the electrical measuring method according to an embodiment of the present application, for example, when the blood is used as the measurement target, a blood coagulation situation or a blood sedimentation situation can be analyzed from the measurement value of the permittivity or impedance. More specifically, for example, a parameter showing characteristics from a plurality of permittivity and/or impedance measurement values received during the analysis period can be derived, and the blood coagulation situation or the blood sedimentation situation can be analyzed based on comparison of the parameter with a reference value that determines a reference of acceleration of blood coagulability or progress of a blood sedimentation process.

Additionally, the present application may also be configured as below.

(1) An electrical measuring container of a biological sample in a liquid phase, including at least:
  a biological sample holding section configured to accommodate a biological sample in a liquid phase and made of a resin; and
  an electrical conductive section fixed to the biological sample holding section,
  wherein, in a state in which a portion of the electrical conductive section is buried in the biological sample holding section, the biological sample holding section and the electrical conductive section are integrally formed with each other.

(2) The electrical measuring container according to (1), wherein the electrical conductive section is integrated with the biological sample holding section through insert molding.

(3) The electrical measuring container according to (1) or (2),
 wherein the electrical conductive section includes at least an electrode section configured to come into contact with the biological sample upon measurement, and a connecting section configured to be electrically connected to an external circuit.

(4) The electrical measuring container according to (3), further including:
 one or more pairs of the electrode sections.

(5) The electrical measuring container according to (3) or (4), wherein the electrode section is included in a portion of an inner wall of the electrical measuring container.

(6) The electrical measuring container according to (5), wherein a connecting section of the biological sample holding section and the electrode section is smoothly formed at the inner wall.

(7) The electrical measuring container according to any one of (3) to (6), wherein the electrode section is disposed a predetermined distance above a portion that becomes a bottom section upon measurement.

(8) The electrical measuring container according to any one of (1) to (7), wherein at least a portion of the electrical conductive section functions as a holding section configured in a manner that the electrical conductive section is disposed at a predetermined place of the biological sample holding section when the biological sample holding section and the electrical conductive section are integrally formed with each other.

(9) The electrical measuring container according to any one of (1) to (8), wherein the biological sample contains a sedimentary ingredient.

(10) The electrical measuring container according to any one of (1) to (9), wherein the biological sample contains a blood ingredient.

(11) The electrical measuring container according to (9),
 wherein biological sample contains the sedimentary ingredient, and
 wherein the electrode section is disposed such that an accumulation sedimentation fraction of the sedimentary ingredient from the portion that becomes the bottom section upon measurement is disposed over a position at which the accumulation sedimentation fraction is equal to or larger than a volume fraction of the sedimentary ingredient.

(12) The electrical measuring container according to any one of (1) to (11), further including:
 a bending section at a portion of the electrical conductive section, the portion being buried in the biological sample holding section.

(13) The electrical measuring container according to any one of (1) to (12), wherein the resin includes one or more kinds of resins selected from polypropylene, polystyrene, acryl, and polysulfone.

(14) The electrical measuring container according to any one of (1) to (13), wherein the electrical conductive section is made of an electrical conductive material including titanium.

(15) The electrical measuring container according to any one of (1) to (14), wherein the electrical measuring container is used to measure permittivity of the biological sample.

(16) The electrical measuring container according to any one of (1) to (15), wherein the electrical measuring container is used to measure impedance of the biological sample.

(17) The electrical measuring container according to (10), wherein the electrical measuring container is used to measure a blood sedimentation situation.

(18) The electrical measuring container according to (10) or (17), wherein the electrical measuring container is used to measure a blood coagulation situation.

(19) An electrical measuring apparatus of a biological sample in a liquid phase, including at least:
 a biological sample holding section configured to accommodate a biological sample in a liquid phase and made of a resin;
 an electrical conductive section, at least a portion of the electrical conductive section being configured to come into contact with the biological sample upon measurement;
 an application unit configured to apply a voltage to the electrical conductive section; and
 a measurement unit configured to measure an electrical property of the biological sample,
 wherein, in a state in which a portion of the electrical conductive section is buried in the biological sample holding section, the biological sample holding section and the electrical conductive section are integrally formed with each other.

(20) An electrical measuring method of a biological sample in a liquid phase used to measure an electrical property of the biological sample using an electrical measuring container of the biological sample in the liquid phase, the electrical measuring container including at least
 a biological sample holding section configured to accommodate a biological sample in a liquid phase and made of a resin, and
 an electrical conductive section fixed to the biological sample holding section,
 wherein, in a state in which a portion of the electrical conductive section is buried in the biological sample holding section, the biological sample holding section and the electrical conductive section are integrally formed with each other.

Since the electrical measuring container 1 according to the present application uses no adhesive agent to fix the biological sample holding section 2 and the electrical conductive section 3, an influence on the biological sample S due to the adhesive agent can be excluded. As a result, the electrical properties of the biological sample S can be precisely measured.

In addition, in the manufacturing process of the electrical measuring container 1 according to the present application, since the biological sample holding section 2 and the electrical conductive section 3 are integrally formed with each other, the adhering process does not have to be separately provided in addition to the forming process of the biological sample holding section 2. As a result, the electrical measuring container 1 can be easily manufactured, and the electrical measuring container 1 can be produced at a low cost in large quantities.

Further, in the electrical measuring container 1 according to the present application, the electrical conductive section 3 is previously fixed to the biological sample holding section 2. For this reason, as the electrical conductive section 3 is used as the electrode, a measurement error due to a difference in insertion amount of the electrodes into the liquid sample can be removed.

As a result, the electrical properties of the biological sample S can be precisely measured.

In addition, as the electrical conductive section 3 is previously fixed to the biological sample holding section 2, the apparatus can be simply configured, and this can contribute to realization of miniaturization of the apparatus or simplification of the manufacturing process, a low cost of the apparatus, and so on.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. An electrical measuring container, comprising:
a biological sample holding section configured to accommodate a biological sample in a liquid phase; and
an electrical conductive section fixed to the biological sample holding section, wherein
the biological sample holding section is integral to the electrical conductive section based on a first portion of the electrical conductive section that is buried in a sidewall of the biological sample holding section,
the first portion which is buried in the sidewall of the biological sample holding section comprises a first electrode,
the first electrode is prevented to extend out of an inner surface of the sidewall of the biological sample holding section,
the first electrode is included in a portion of an inner wall of the biological sample holding section,
the first electrode is integrated in and extends along a portion of the sidewall of the biological sample holding section,
the first electrode, which is prevented to extend out of the inner surface of the sidewall, is at a first distance away from a bottom of the biological sample holding section and at a second distance away from a top of the biological sample holding section,
each of the first distance and the second distance is greater than 0, and
the first distance is different from the second distance.

2. The electrical measuring container according to claim 1, wherein the electrical conductive section is integrated with the biological sample holding section by an insert molding process.

3. The electrical measuring container according to claim 1, wherein the electrical conductive section includes:
the first electrode configured to contact the biological sample upon measurement; and
a connecting section configured to electrically connect to an external circuit.

4. The electrical measuring container according to claim 3, further comprising at least one pair of electrodes including the first electrode and a second electrode.

5. The electrical measuring container according to claim 3, wherein at least a part of the connecting section of the electrical conductive section is at the inner wall.

6. The electrical measuring container according to claim 3, wherein
the first electrode is at a third distance above a portion of the biological sample holding section, and
the portion of the biological sample holding section becomes a bottom section upon measurement.

7. The electrical measuring container according to claim 1, wherein
a connecting section of the electrical conductive section is configured to function as a holding section, and
the holding section is configured such that the electrical conductive section is at a specific place of the biological sample holding section.

8. The electrical measuring container according to claim 1, wherein the biological sample contains a sedimentary ingredient.

9. The electrical measuring container according to claim 8, wherein the first electrode is above a position at which an accumulation sedimentation fraction of the sedimentary ingredient is equal to or larger than a volume fraction of the sedimentary ingredient.

10. The electrical measuring container according to claim 1, wherein the biological sample contains a blood ingredient.

11. The electrical measuring container according to claim 10, wherein the electrical measuring container is configured to measure a blood sedimentation situation.

12. The electrical measuring container according to claim 10, wherein the electrical measuring container is configured to measure a blood coagulation situation.

13. The electrical measuring container according to claim 1, further comprising a bending section at a second portion of the electrical conductive section, wherein the second portion is buried in the biological sample holding section.

14. The electrical measuring container according to claim 1, wherein
the biological sample holding section is a resin, and
the resin includes at least one of polypropylene, polystyrene, acryl, or polysulfone.

15. The electrical measuring container according to claim 1, wherein
the electrical conductive section comprises an electrical conductive material, and
the electrical conductive material includes titanium.

16. The electrical measuring container according to claim 1, further comprising a measurement unit configured to measure a permittivity of the biological sample.

17. The electrical measuring container according to claim 1, further comprising a measurement unit configured to measure an impedance of the biological sample.

18. The electrical measuring container according to claim 1, further comprising a bending section at a second portion of the electrical conductive section, wherein
the bending section is bent in a determined shape, and
an entire bending section is embedded in the sidewall of the biological sample holding section.

19. An electrical measuring apparatus, comprising:
a biological sample holding section configured to accommodate a biological sample in a liquid phase;
an electrical conductive section, wherein a first portion of the electrical conductive section is configured to contact the biological sample upon measurement;
an application unit configured to apply a voltage to the electrical conductive section; and
a measurement unit configured to measure an electrical property of the biological sample, wherein
the biological sample holding section is integral to the electrical conductive section based on a second portion of the electrical conductive section that is buried in a sidewall of the biological sample holding section,
the second portion which is buried in the sidewall of the biological sample holding section comprises a single electrode, wherein the single electrode is prevented to extend out of an inner surface of the sidewall of the biological sample holding section, the single electrode is integrated in and extends along a portion of the sidewall of the biological sample holding section, the single electrode, which is prevented to extend out of the inner surface of the sidewall, is at a first distance away from a bottom of the biological sample holding section and at a second distance away from a top of the biological sample holding section, each of the first distance and the second distance is greater than 0, and the first distance is different from the second distance.

20. An electrical measuring method, comprising:

accommodating a biological sample in a liquid phase in a biological sample holding section, wherein the biological sample holding section is integral to an electrical conductive section based on a portion of the electrical conductive section that is buried in a sidewall of the biological sample holding section, the portion of the electrical conductive section which is buried in the sidewall of the biological sample holding section comprises an electrode, the electrode is prevented to extend out of an inner surface of the sidewall of the biological sample holding section, the electrode is integrated in and extends along a portion of the sidewall of the biological sample holding section, the electrode is included in a portion of an inner wall of the biological sample holding section, the electrode, which is prevented to extend out of the inner surface of the sidewall, is at a first distance away from a bottom of the biological sample holding section and at a second distance away from a top of the biological sample holding section, each of the first distance and the second distance is greater than 0, and the first distance is different from the second distance; and measuring an electrical property of the biological sample.

* * * * *